(12) United States Patent  
Ozaki (10) Patent No.: US 8,693,280 B2  
(45) Date of Patent: Apr. 8, 2014

(54) ULTRASONIC DIAGNOSTIC APPARATUS (75) Inventor: Hiroshi Ozaki, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 406 days.

(21) Appl. No.: 13/122,497

(22) PCT Filed: Oct. 7, 2009

(86) PCT No.: PCT/JP2009/067487  
§ 371 (c)(1),  
(2), (4) Date: Apr. 4, 2011

(87) PCT Pub. No.: WO2010/041683  
PCT Pub. Date: Apr. 15, 2010

(65) Prior Publication Data  
US 2011/0182137 A1  Jul. 28, 2011

(30) Foreign Application Priority Data  
Oct. 7, 2008 (JP) .................. 2008-260372

(51) Int. Cl.  
*A61B 8/00* (2006.01)

(52) U.S. Cl.  
USPC ............................. 367/7; 600/446

(58) Field of Classification Search  
USPC ........................... 600/446; 367/7  
See application file for complete search history.

(56) References Cited

U.S. PATENT DOCUMENTS

| | | | | |
|---|---|---|---|---|
| 6,238,341 B1 * | 5/2001 | Mullen | ......... | 600/437 |
| 6,468,212 B1 * | 10/2002 | Scott et al. | ......... | 600/437 |
| 6,674,879 B1 * | 1/2004 | Weisman et al. | ......... | 382/128 |
| 7,022,075 B2 * | 4/2006 | Grunwald et al. | ......... | 600/446 |

FOREIGN PATENT DOCUMENTS

| | | |
|---|---|---|
| JP | 2002-248099 | 9/2002 |
| JP | 2005-270317 | 10/2005 |
| JP | 2007-260188 | 10/2007 |
| JP | 2008-029468 | 2/2008 |

* cited by examiner

*Primary Examiner* — Mark Hellner  
(74) *Attorney, Agent, or Firm* — Brundidge & Stanger, P.C.

(57) ABSTRACT

An ultrasonic diagnostic apparatus provided with an ultrasonic image measuring unit configured to measure an ultrasonic image of an object to be examined, a display unit configured to display the ultrasonic image, an input unit configured to input parameters for controlling the ultrasonic image measuring unit and the display unit, and a control unit configured to control the ultrasonic image measuring unit and the display unit by means of the parameters.

The control unit is characterized by generating first switch information for inputting relating to a first control parameter included in the parameters, controlling the display unit to display the first switch information, selecting the first control parameter from the first switch information and inputting thereof, generating second switch information relating to a second control parameter which is the item next to the first control parameter, and controlling the display unit to display the second switch information.

6 Claims, 12 Drawing Sheets

| BUTTON TYPE | BUTTON FORMAT |
|---|---|
| PUSH TYPE |  |
| TOGGLE TYPE |  |
| ENCODER TYPE |  |

FIG. 9

FIG.10

ULTRASONIC DIAGNOSTIC APPARATUS

FIELD OF THE INVENTION

The present invention relates to an ultrasonic diagnostic apparatus capable of displaying a menu provided with a plurality of operation buttons on a touch panel on a screen and executing various operations displayed therein.

DESCRIPTION OF RELATED ART

In recent years, ultrasonic diagnostic apparatuses are provided with a touch panel switch on a screen on which an ultrasonic image is to be displayed. The touch panel switch is configured, for example as transparent except one or a plurality of switches so that an ultrasonic image displayed on the screen can be seen through the panel as the background (for example, refer to Patent Document 1).

By the switch of the touch panel, a plurality of conditions are set by the following procedure when it is assumed, for example that the distance between two arbitrary points on an image is to be measured.

First, an operator searches the switch for distance measurement from the menu displayed on the touch panel, and touches or holds his/her hand over the switch. In this manner, the first condition of distance measurement is determined.

Next, in order to set the position of each cursor showing a starting point and an ending point for measuring the distance between the two points, the operator traces the touch panel with his/her finger or moves the cursor to a desired position using a trackball. In this manner, the second condition of distance measurement is determined.

PRIOR ARTS

Patent Document 1: JP-A-2002-248099

However, the touch panel of the above-mentioned conventional technique requires the operator to quickly move the line of sight and search for the switch or the input unit in order to input the second condition after determining the first condition by the condition setting of the command switch, which makes the complicated for the operator.

In this manner, the problem still remains while the operator desires to determine the second condition without changing the line of sight after determining the first condition.

Given this factor, the objective of the present invention is to provide an ultrasonic diagnostic apparatus capable of executing condition setting by a command switch without requiring the operator to change the light of sight.

BRIEF SUMMARY OF THE INVENTION

The representative configuration of the ultrasonic diagnostic apparatus related to the present invention comprises:
an ultrasonic image measuring unit configured to measure an ultrasonic image of an object to be examined;
a display unit configured to display the ultrasonic image;
an input unit configured to input parameters for controlling the ultrasonic image measuring unit and the display unit; and
a control unit configured to control the ultrasonic measuring unit and the display unit by the parameters,
wherein the control unit generates first switch information for inputting a first control parameter from among the parameters, causes the display unit to display the first switch information, inputs the first control parameter by selecting it from the first switch information, generates second switch information to be the item next to the first control parameter, and causes the display unit to display the second switch information.

The control unit generates a first switch information for inputting a first control parameter from among the parameters, causes the display unit to display the first switch information, inputs the first control parameter by selecting it from the first switch information, generates a second switch information to be the item next to the first control parameter, and causes the display unit to display the second switch information. In this manner, condition setting by a command switch can be executed without requiring an operator to change the line of sight.

Effect of the Invention

In accordance with the present invention, it is possible to provide an ultrasonic diagnostic apparatus capable of executing condition setting by a command switch without requiring an operator to change the line of sight.

DETAILED DESCRIPTION OF THE INVENTION

An embodiment of the ultrasonic diagnostic apparatus related to the present invention will be described below in detail referring to the attached diagrams. In the following description, the same function parts are represented by the same reference numerals, and the duplicative description thereof is omitted.

Figure 1:
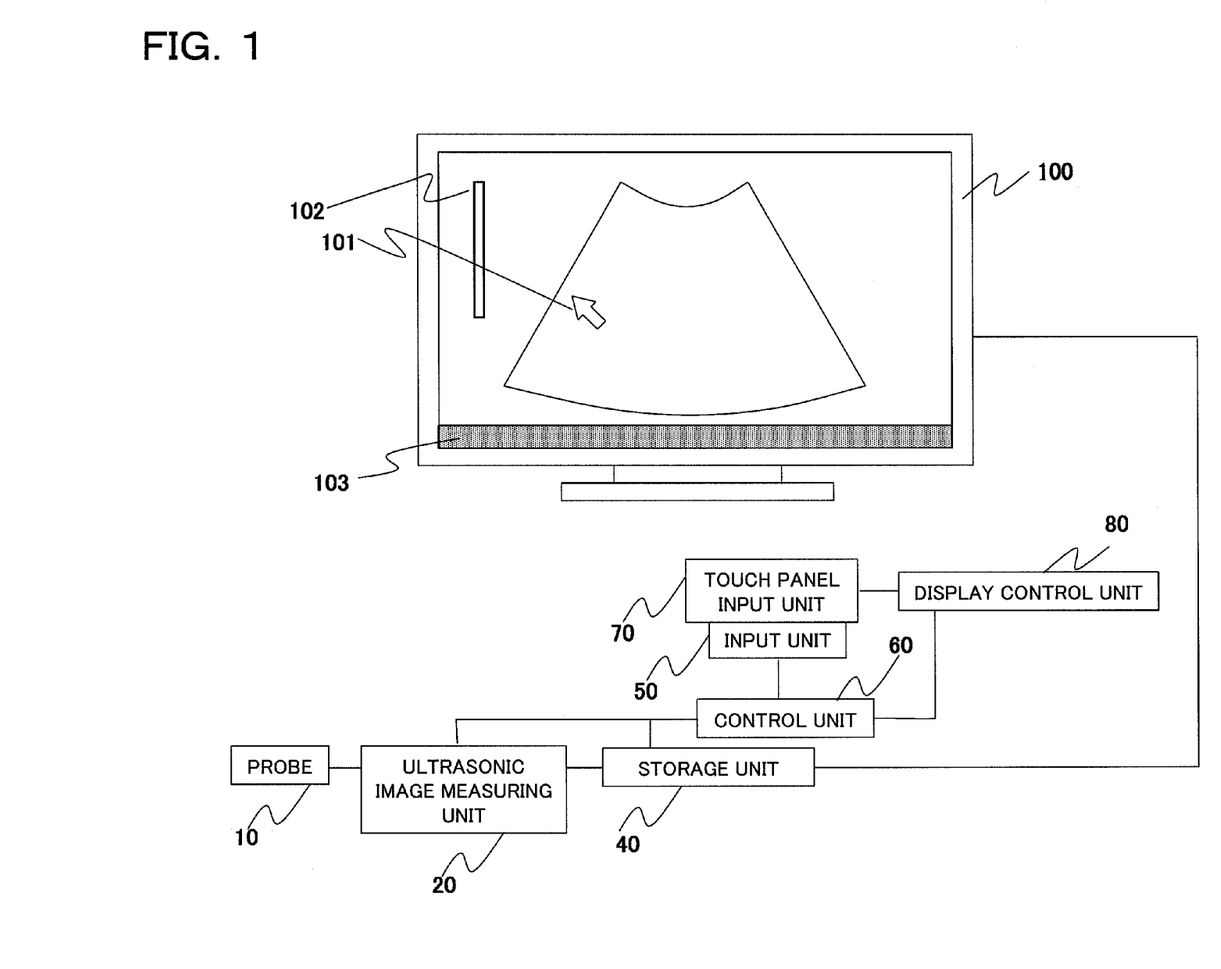
FIG. 1 is a block diagram of an ultrasonic diagnostic apparatus related to an embodiment of the present invention.

FIG. 1 shows a block configuration of the ultrasonic diagnostic apparatus related to an embodiment of the present invention.

The ultrasonic diagnostic apparatus of the present embodiment comprises probe 10, ultrasonic image measuring unit 20 connected to probe 10 while being available for transmission and reception of signals, storage unit 40 connected to ultrasonic image measuring unit 20 while being available for transmission and reception of signals, first display unit 100 connected to storage unit 40 while being available for transmission and reception of signals, input unit 50, control unit 60 connected to input unit 50 while being available for transmission and reception of signals, second display unit 70 mounted to input unit 50, and display control unit 80 connected to first display unit 100 and second display unit 70 while being available for transmission and reception of signals.

Probe 10 transmits ultrasonic waves to an object by being applied to the object and receives the reflected echo signals from the object. Ultrasonic image measuring unit 20 executes signal processing such as phasing on the reflected echo signals, and measures an ultrasonic image including brightness (B) mode image, motion (M) mode image, Doppler (D) mode image and elastic (E) mode image. First display unit 100 displays the measured ultrasonic image.

Input unit 50 inputs the parameters for controlling ultrasonic image measuring unit 20 and first display unit 100. Control unit 60 controls ultrasonic measuring unit 20 and first display unit 100 by the parameters inputted by input unit 50. Display control unit 80 inputs the first control parameter by an operator to second display unit 70, determines the input of the first control parameter, generates the menu for setting the second control parameter which is to be the item next to the determined first control parameter on a part of the first display unit 100, controls the display of the generated menu on first display unit 100, and controls the display of a switch being corresponded to the generated menu on the second display unit 70.

Here, for example the first control parameter indicates the kind of execution program of the operator's desired measurement or analysis such as variety of measurement conditions that are a B-mode image, M-mode image, D-mode image, E-mode image, etc. or application such as a body mark and distance measurement. The second parameter is the condition to be set next to the kind of execution program for a desired measurement or analysis, for example the body mark for selecting the region to which an ultrasonic probe should be applied, for example the front or the side of an abdominal region.

Also, while the case that control parameters are set in two stages such as the first and the second parameters is exemplified here, a third control parameter or a fourth control parameter may further be set thereto according to need, for example for the case of 3-dimensional measurement.

On first display unit 100, for example B-mode image 101 acquired using a convex-type probe and gray scale 102 showing luminance range of the displayed B-mode image are displayed. Display area 103 is the area for displaying function keys of a touch panel related to the present invention, and will be referred to as function-key display area 103.

(First Embodiment)

Figure 2A:
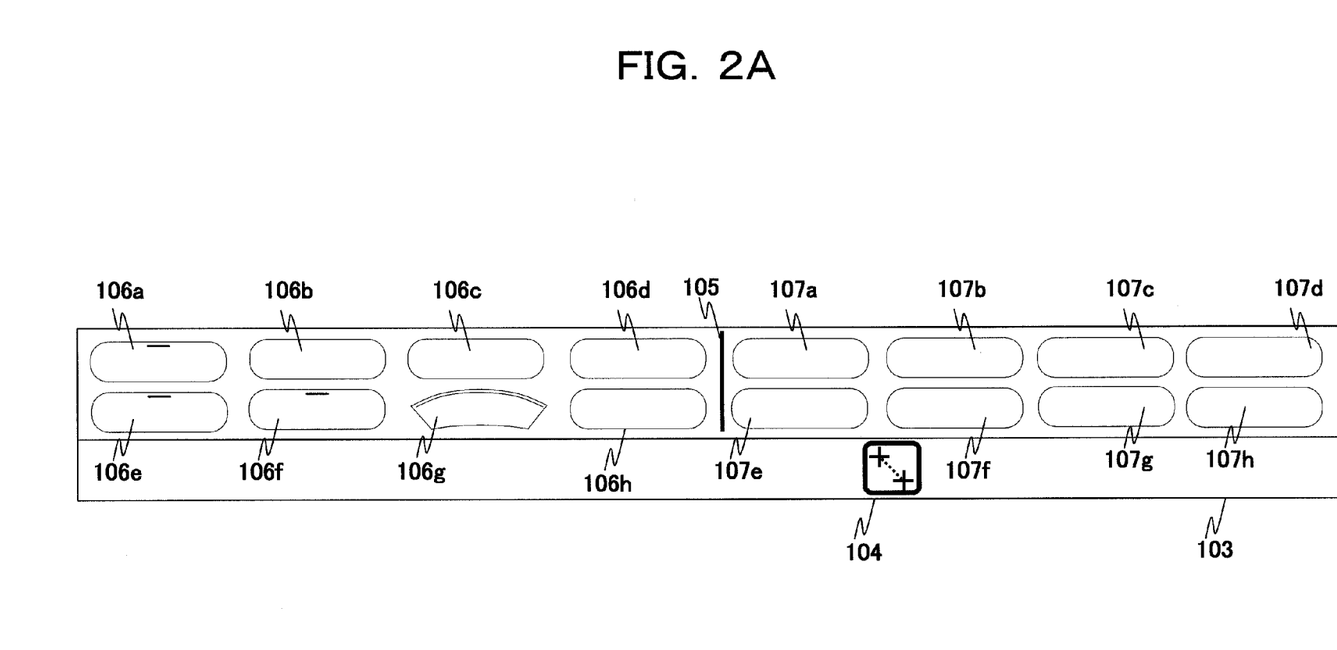
FIG. 2A is for explaining an example of the key arrangement in a first embodiment related to the ultrasonic diagnostic apparatus shown in FIG. 1.
Figure 2B:
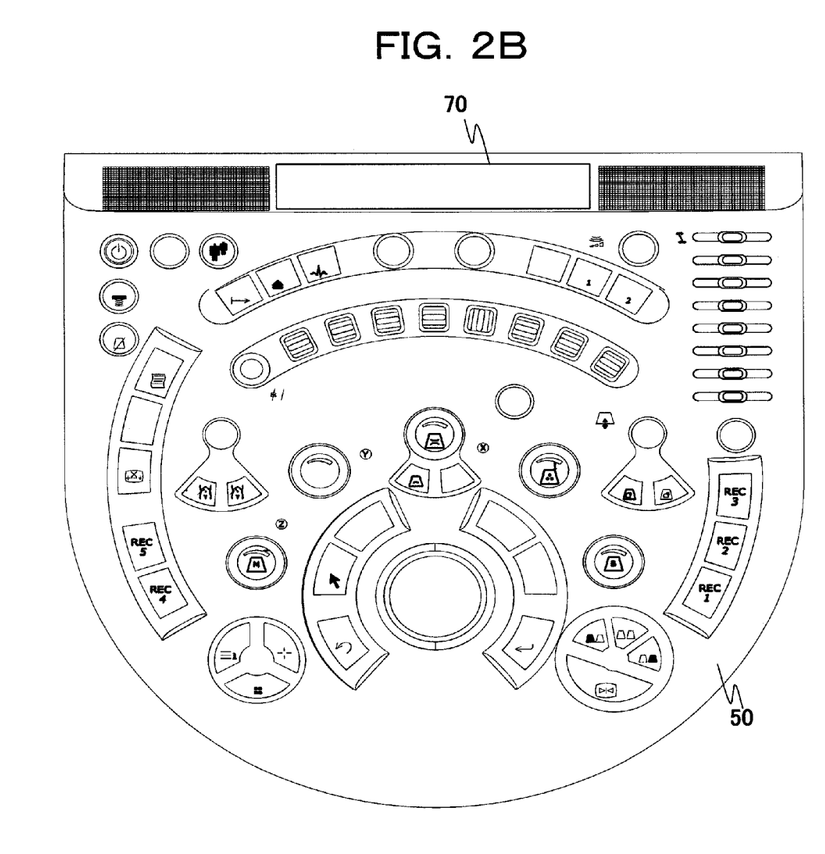
FIG. 2B is for explaining an example of the key arrangement in the first embodiment related to the ultrasonic diagnostic apparatus shown in FIG. 1.
Figure 2C:
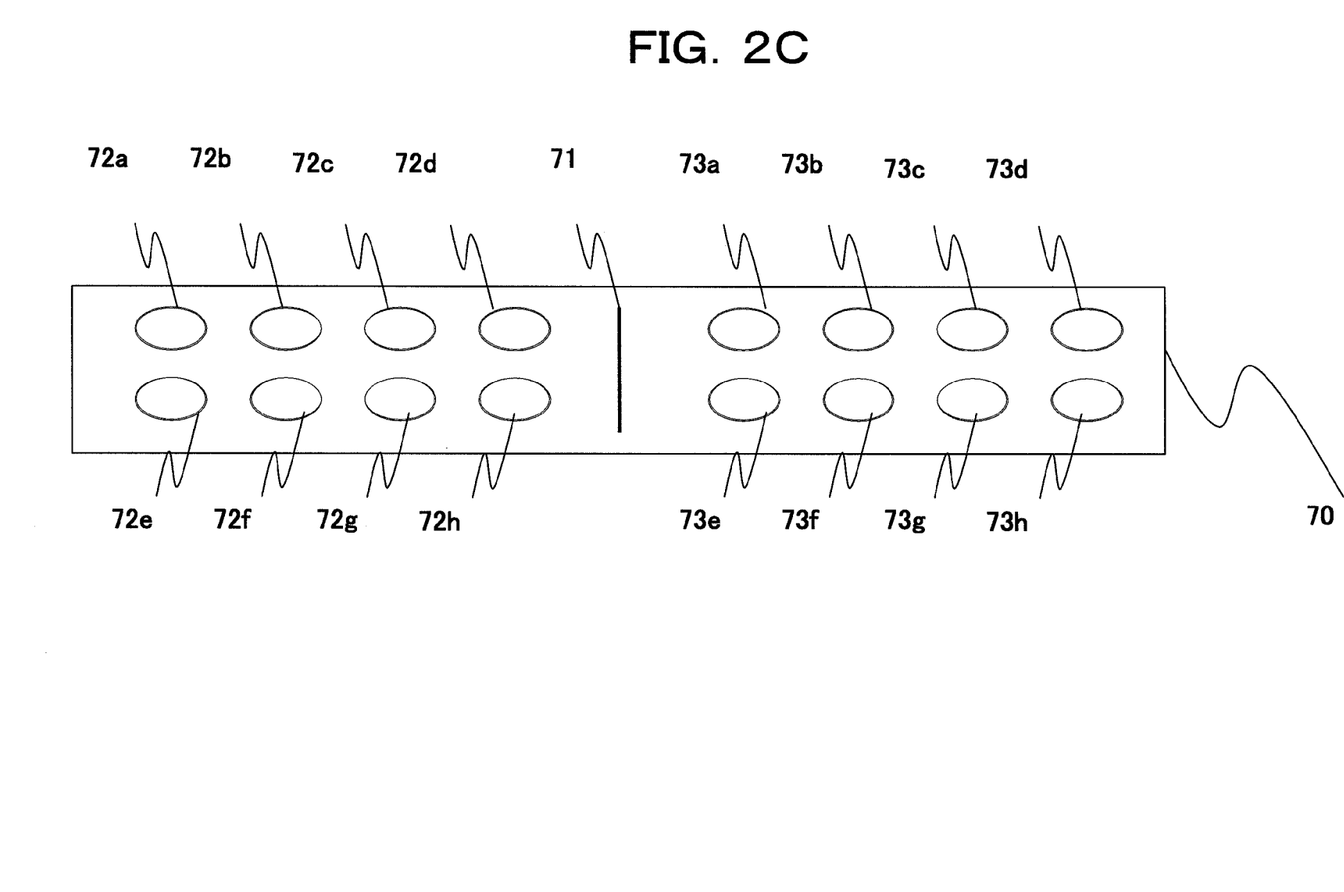
FIG. 2C is for explaining an example of the key arrangement in the first embodiment related to the ultrasonic diagnostic apparatus shown in FIG. 1.
Figure 3:
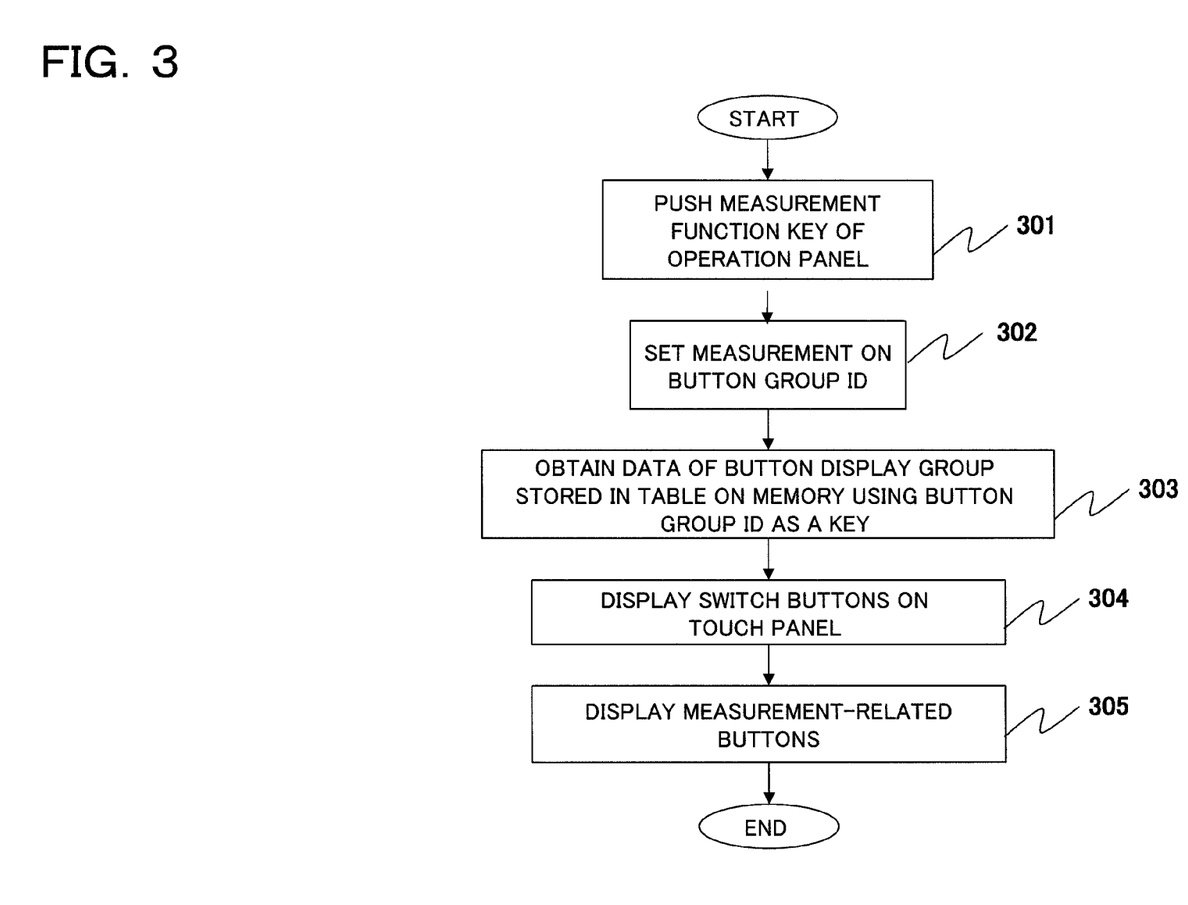
FIG. 3 is a flowchart for explaining an example of operation in the first embodiment.

The first embodiment is an example wherein arrangement of function keys displayed on function-key display area 103 of first display unit 100 and arrangement of function keys displayed on second display unit 70 are displayed by one-to-one correspondence, and an example that measurement is set on the first control parameter is described using FIG. 2 and FIG. 3.

FIG. 2 is for explaining an example of key arrangement in the first embodiment related to the ultrasonic diagnostic apparatus shown in FIG. 1.

FIG. 2A shows function-key display area 103 of first display unit 100, FIG. 2B shows arrangement of second display unit (touch panel) on input unit 50, and FIG. 2C is an enlarged view of second display unit 70 shown in FIG. 2B.

On function-key display area 103, as shown in FIG. 2A, measurement-type switch 104 indicating distance measurement, centerline 105 indicating the center of key arrangement, respective keys 106a~106h disposed from centerline 105 to the left, and respective keys 107a~107h from centerline 105 to the right.

Display of centerline 71, keys 72a~72h and 73a~73h of second display unit 70 in FIG. 2B are controlled by display control unit 80 so as to correspond to centerline 105, keys 106a~106h and 107a~107h shown in function-key display area 103.

A concrete example of the display control will be as shown in chart 1 when FIG. 2C is corresponded to FIG. 2A.

Display control unit 80 executes display control so as to make measurement of key 106e to be corresponded to key 72e. In concrete terms, key information on measurement function of key 106e is read out by control unit 60 to storage unit 40, control unit 60 causes display control unit 80 to analyze that the key information is the measurement function, and display control unit 80 reflects the analyzed key information to key 72a and displays the information. This procedure is executed as shown in FIG. 3 by the program of a computer which configures control unit 60 and display control unit 80.

FIG. 3 is a flowchart explaining an example of the operation to be carried out in the first embodiment.

An operator pushes a measurement function key of second display unit 70 (an operation key in conjunction with the touch panel). In concrete terms, when measurement key 104 (caliper, trace) of the operation panel is pushed at the time of executing measurement, display of the touch panel is switched to the content for measurement after measurement function is executed via the operation panel or the touch panel, and the button for measurement is displayed by the following steps (step 301).

Control unit 60 sets the measurement to button group ID (step 302).

Control unit 60 obtains data of the button display group stored in the table on storage unit 40 such as a memory by using button group ID as a key (step 303).

Display control unit 80 switches and sets the buttons on second display unit 70 (touch panel) (step 304).

Display control unit 80 displays on second display unit 70 a measurement-related button to be the second condition of measurement setting (step 305).

As mentioned above, in accordance with the ultrasonic diagnostic apparatus of the first embodiment, display control unit 80 determines the input of the first control parameter on second display unit 70 executed by an operator, generates the menu for setting the second control parameter which is to be the item next to the determined first control parameter on a part of first display unit 100, executes display control of the generated menu on the first display unit 100, and executes display control on the second display unit 70 by corresponding the menu to the switch. As for the subject of display control, the first control parameter is set as measurement mode including distance between predetermined points in an image, area and volume, and the second control parameter is set as the menu for selecting the kind of measurement mode.

In this way, the operator can set the conditions by a command switch without changing his/her line of sight. Also, characteristic effect of the first embodiment is that an unallotted key is displayed on first display unit 100 and first display unit 70 respectively by setting an unallotted key on first display unit 100 and on a touch panel button of second display unit 70. In this example, 16 buttons are displayed so as to help the operator to easily correspond them to the 16 keys of the operation panel. In this manner, the operator can set conditions more intuitively.

CHART 1

| FIG. 2(c)<br>Centerline 71 | FIG. 2(a)<br>Centerline 105 |
|---|---|
| key 72a | Key 106a |
| Key 72b | Key 106b |
| Key 72c | Key 106c |
| Key 72d | Key 106d |
| Key 72e | Key 106e |
| Key 72f | Key 106f |
| Key 72g | Key 106g |
| Key 72h | Key 106h |
| Key 73a | Key 107a |
| Key 73b | Key 107b |
| Key 73c | Key 107c |
| Key 73d | Key 107d |
| Key 73e | Key 107e |
| Key 73f | Key 107f |
| Key 73g | Key 107g |
| Key 73h | Key 107h |

(Second Embodiment)

The second embodiment is an example that arrangement of function keys to be displayed on function-key display area 103 of first display unit 100 and arrangement of function keys to be displayed on second display unit 70 are displayed by one-on-one correspondence, and the example that a body mark is set on the first control parameter will be described using FIG. 4 and FIG. 5.

Figure 4:
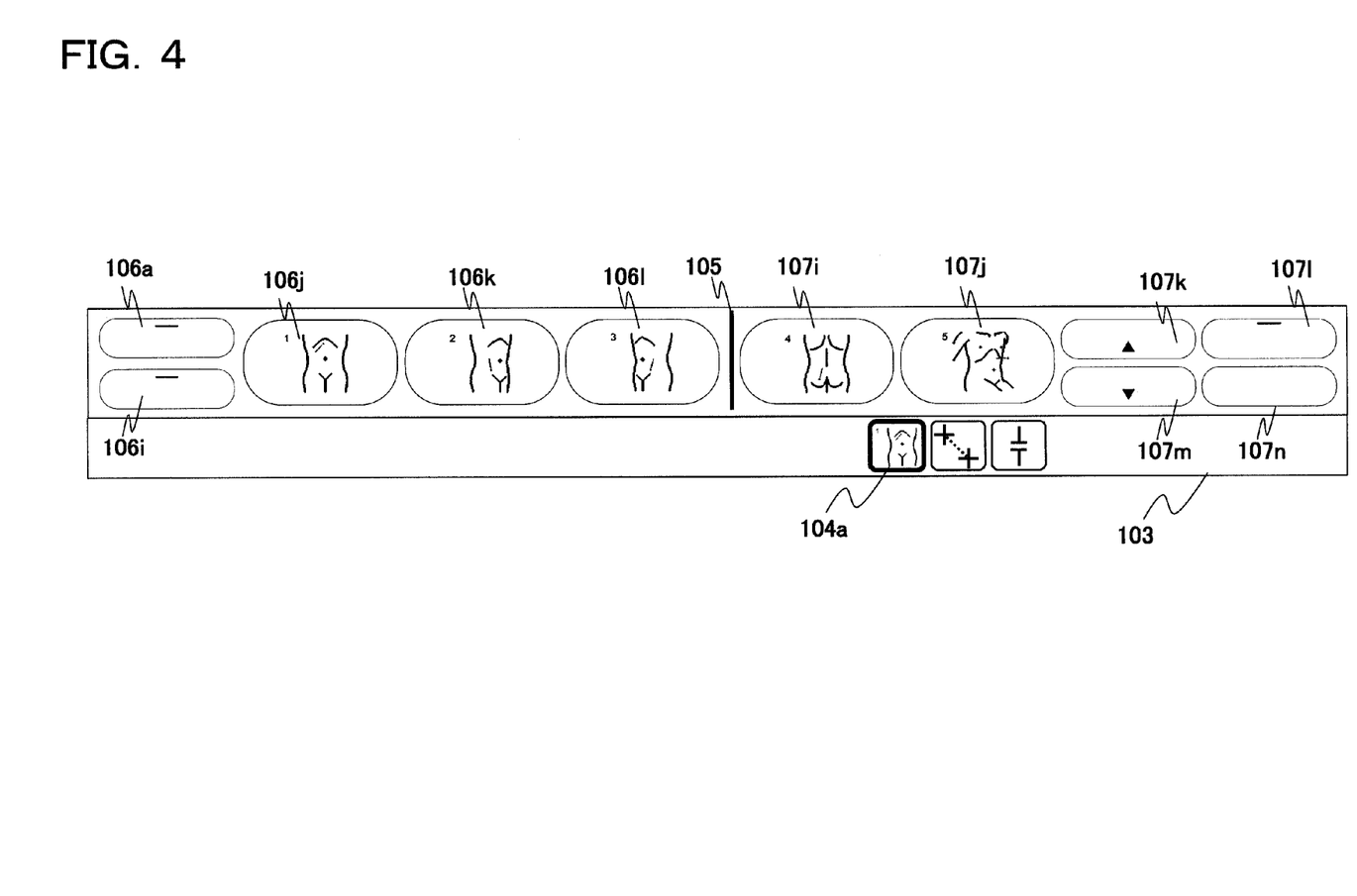
FIG. 4 is for explaining an example of the key arrangement in a second embodiment related to the ultrasonic diagnostic apparatus shown in FIG. 1.

FIG. 4 is for explaining an example of key arrangement in the second embodiment related to the ultrasonic diagnostic apparatus shown in FIG. 1.

FIG. 4 shows function-key display area 103 of first display unit 100.

On function-key display area 103, as shown in FIG. 4, body-mark type switch 104a indicating the type of a body mark, centerline 105 indicating the center of key arrangement, respective keys 106a, 106i~106l from centerline 105 to the left and respective keys 107i~107n from the centerline 105 to the right are displayed. Display of centerline 71 and the respective keys of second display unit 70 are controlled by display control unit 80 so as to correspond to centerline 105 and the respective keys shown on function-key display area 103.

Display control unit 80 executes display control to set key 72a to be corresponded to a body mark of key 106a. In concrete terms, key information of body-mark function of key 106a is read out by control unit 60 to storage unit 40, control unit 60 causes display control unit 80 to analyze that the key information is the body-mark function, and display unit 80 reflects the analyzed key information to key 72a and displays the information. This procedure is executed as shown in FIG. 5 by the program of a computer which configures control unit 60 and display control unit 80.

Figure 5:
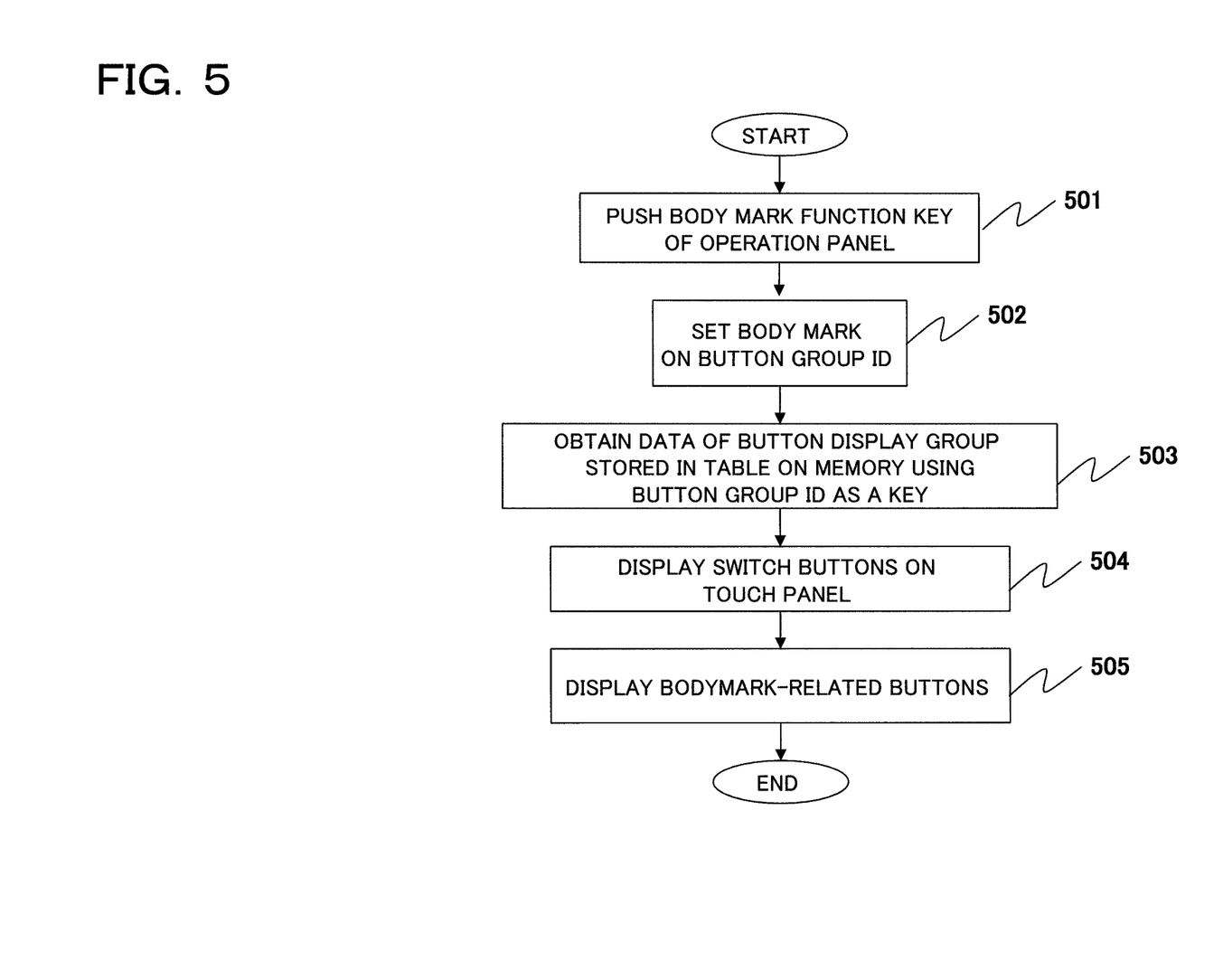
FIG. 5 is a flowchart for explaining an example of operation in the second embodiment.

FIG. 5 is a flowchart for explaining an operation example of the second embodiment.

The operator pushes body-mark function key 104a of second display unit 70 (touch panel). In concrete terms, when the operator pushes the button of a body mark on second display unit 70 (touch panel), the operation related to the body mark is executed via the operation panel or touch panel, the touch panel display is switched to the content related to the body mark, and the button for the body mark is displayed.

The body-mark display on second display 70 (touch panel) is switched by the steps below (step 501).

Control unit 60 sets a body mark on button group ID (step 502).

Control unit 60 obtains data of the button display group stored in the table on storage unit 40 such as a memory by using button group ID as a key (step 503).

Display control unit 80 sets a switch function on the button in second display unit 70 (touch panel) (step 504).

Display control unit 80 displays a measurement-related button to be the second condition for the body-mark setting on second display unit 70 (step 505).

As mentioned above, in accordance with the ultrasonic diagnostic apparatus of the second embodiment, display unit 80 determines the input of the first control parameter on second display unit 70 executed by the operator, generates the menu for setting a second control parameter which is to be the item next to the determined first control parameter on a part of the first display unit 100, controls the display of the generated menu on first display unit 100, and controls the display of the switch and the generated menu being corresponded to each other on the second display unit 70.

As for the object of display control, the first control parameter is set as a body mark, and the second control parameter is set as the menu for selecting the kind of the body mark.

In this manner, the operator can set the conditions by a command switch without changing his/her line of sight. Also, characteristic effect of the second embodiment is that the enlarged display setting in first display unit 100 is also reflected to the touch panel button of second display unit 70. In this example, 16 buttons are displayed so as to help the operator to easily correspond them to the 16 keys of the operation panel. In this manner, the operator can set conditions more intuitively.

(Third Embodiment)

The third embodiment is an example that arrangement of function keys to be displayed on function-key display area 103 of first display unit 100 and arrangement of function keys to be displayed on second display unit 70 are displayed by one-on-one correspondence, and the example that Doppler measurement is set as the first control parameter will be described using FIG. 6 and FIG. 7.

Figure 6:
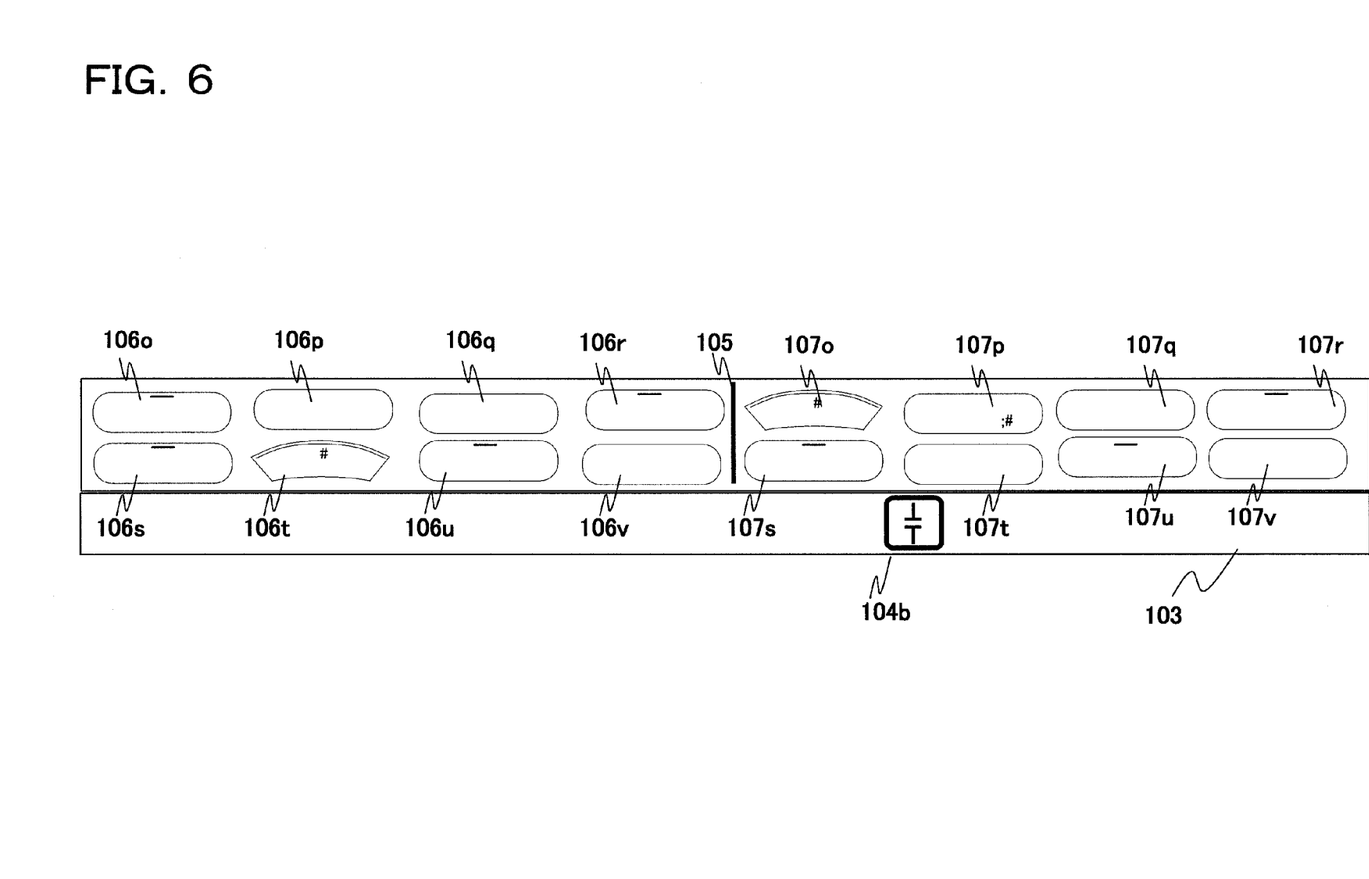
FIG. 6 is for explaining an example of the key arrangement in a third embodiment related to the ultrasonic diagnostic apparatus shown in FIG. 1.

FIG. 6 is for explaining an example of key arrangement in the third embodiment related to the ultrasonic diagnostic apparatus shown in FIG. 1.

FIG. 6 shows function-key display area 103 of first display unit 100.

On function-key display area 103, as shown in FIG. 6, Doppler measurement switch 104b indicating Doppler measurement, centerline 105 indicating the center of key arrangement, respective keys 106o~106v from centerline 105 to the left and respective keys 107o~107v from the centerline 105 to the right are displayed. Display of centerline 71 and the respective keys of second display unit 70 are controlled by display control unit 80 so as to correspond to centerline 105 and the respective keys shown in function-key display area 103.

As in the first and the second embodiments, display control unit 80 controls display arrangement of the function keys to be displayed on function key display area 103 of first display unit 100 and arrangement of the function keys to be displayed on second display unit 70 to make them to be in conjunction with Doppler measurement. This procedure is executed as shown in FIG. 7 by the program of a computer which configures control unit 60 and display control unit 80.

Figure 7:
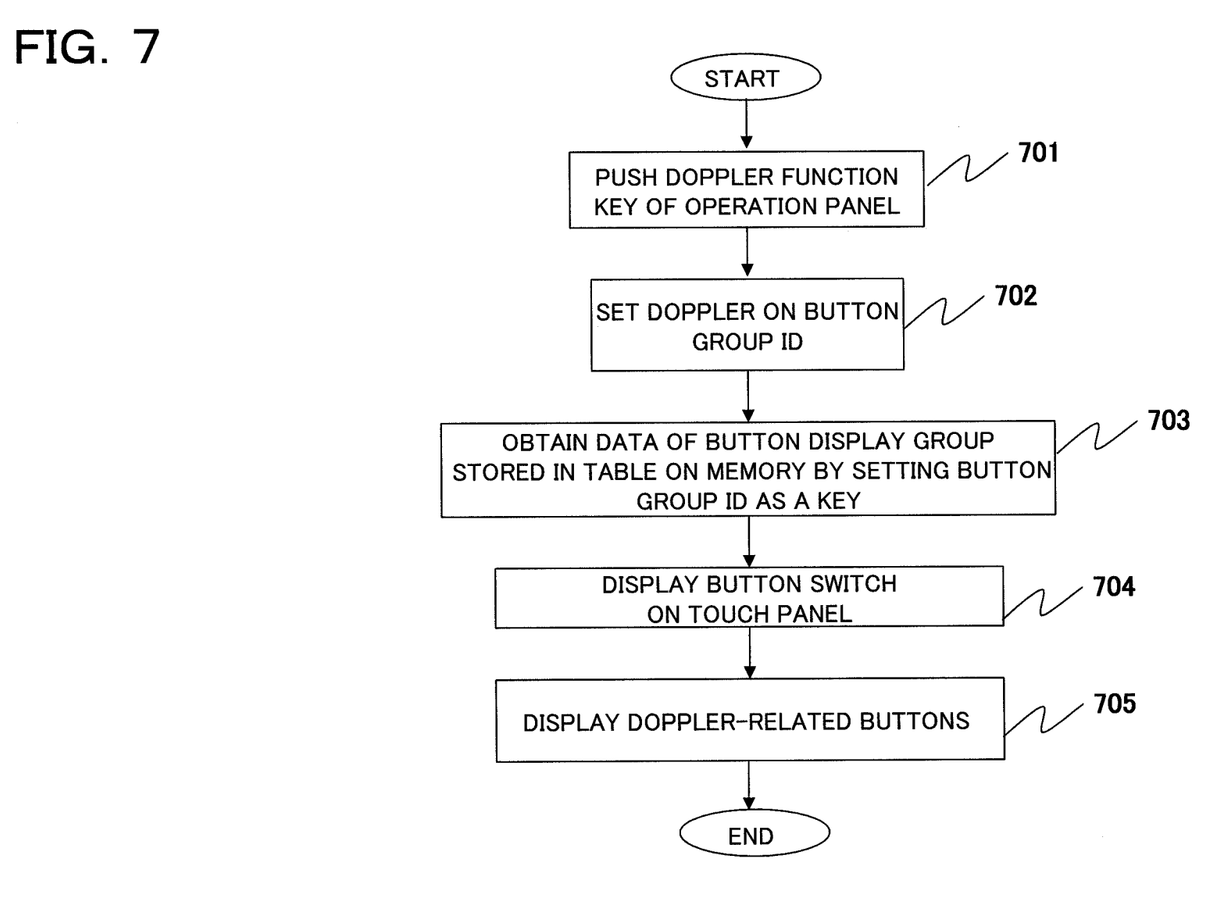
FIG. 7 is a flowchart for explaining an example of operation in the third embodiment.

FIG. 7 is a flowchart for explaining an example of operation in the third embodiment.

The operator pushes execution key 104b of Doppler function in second display unit 70 (touch panel). In concrete terms, when body-mark button on second display unit 70 (touch panel) is pushed by the operator, a PW-mode key of the operation panel is also pushed, display of the touch panel is switched to the content for Doppler mode, and the button for Doppler function is displayed.

The Doppler function display on second display unit 70 (touch panel) is switched by the steps below (step 701).

Control unit 60 sets Doppler function on button group ID (step 702).

Control unit 60 obtains data of the button display group stored in the table on storage unit 40 such as a memory by using button group ID as a key (step 703).

Display control unit 80 executes switch setting of a button on second display unit 70 (touch panel) (step 704).

Display control unit 80 displays a measurement-related button to be the second condition for Doppler-function setting on second display unit 70 (step 705).

As mentioned above, in accordance with the ultrasonic diagnostic apparatus of the third embodiment, display unit 80 determines the input of the first control parameter on second display unit 70 executed by the operator, generates the menu for setting a second control parameter which is to be the item next to the determined first control parameter on a part of the first display unit 100, controls the display of the generated menu on first display unit 100, corresponds the menu to the switch and displays the corresponded menu and the switch on second display unit 70.

As for the object of display control, the first control parameter is set as Doppler mode, and the second control parameter is set as the menu for selecting setting condition of the Doppler mode.

In this way, the operator can set the conditions by a command switch without changing his/her line of sight. Also, characteristic effect of the third embodiment is that the display setting of intrinsic parameter of Doppler measurement on first display unit 100 is reflected also to the touch panel button of second display unit 70. In this example, by displaying the button of the threshold-value level or speaker volume, the operator can easily recognize the correspondence between the buttons and the keys on the operation panel. In this manner, the operator can set conditions more intuitively.

(Fourth Embodiment)

The fourth embodiment is an example that arrangement of function keys to be displayed on function-key display area 103 of first display unit 100 and arrangement of function keys to be displayed on second display unit 70 are displayed by one-on-one correspondence, and will be described using FIG. 8 and FIG. 9.

Figure 8:
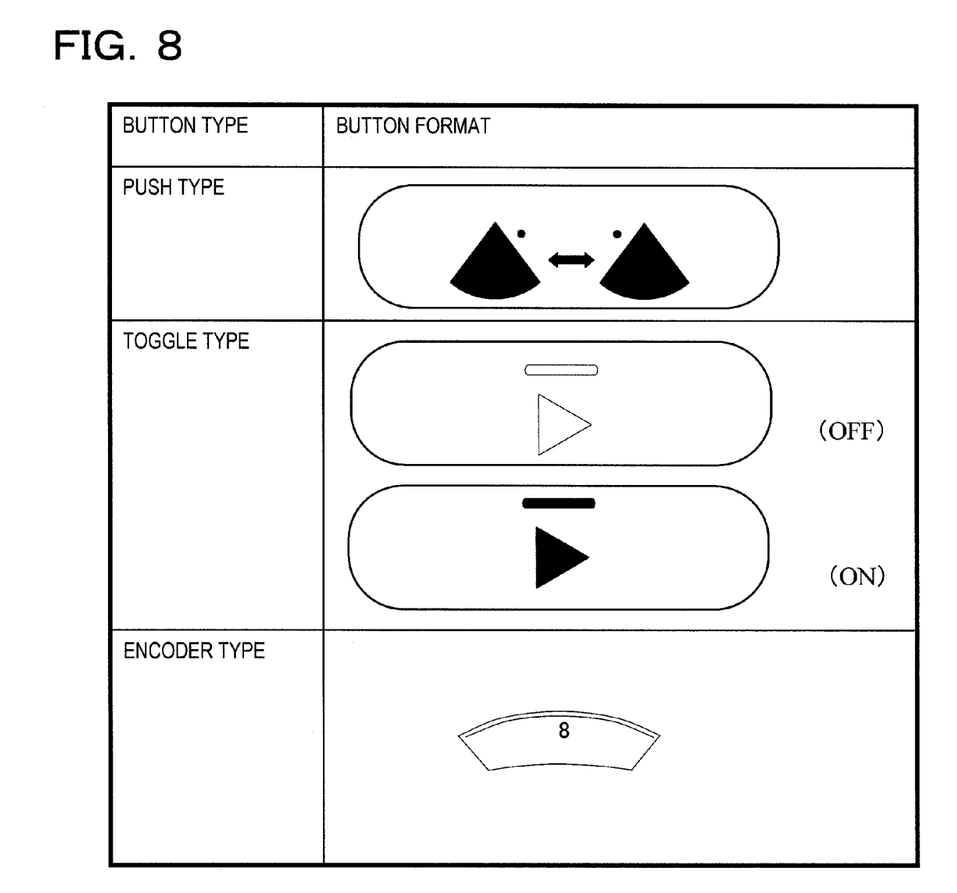
FIG. 8 is for explaining an example of the key arrangement in a fourth embodiment related to the ultrasonic diagnostic apparatus shown in FIG. 1.

FIG. 8 is for explaining a key display example in the fourth embodiment of the ultrasonic diagnostic apparatus shown in FIG. 1. The keys to be used here can be classified broadly into 3 kinds of push type, toggle type and encoder type.

Push type key is for executing a certain function such as a mirror-reversed image button. Toggle type key is for clearly specifying ON/OFF of a switch like a moving-image continuous play button. Encoder type key is for switching the value for a certain function of the device, for example a B-mode gray map switch button, by executing encoder operation on a touch panel.

Figure 9:
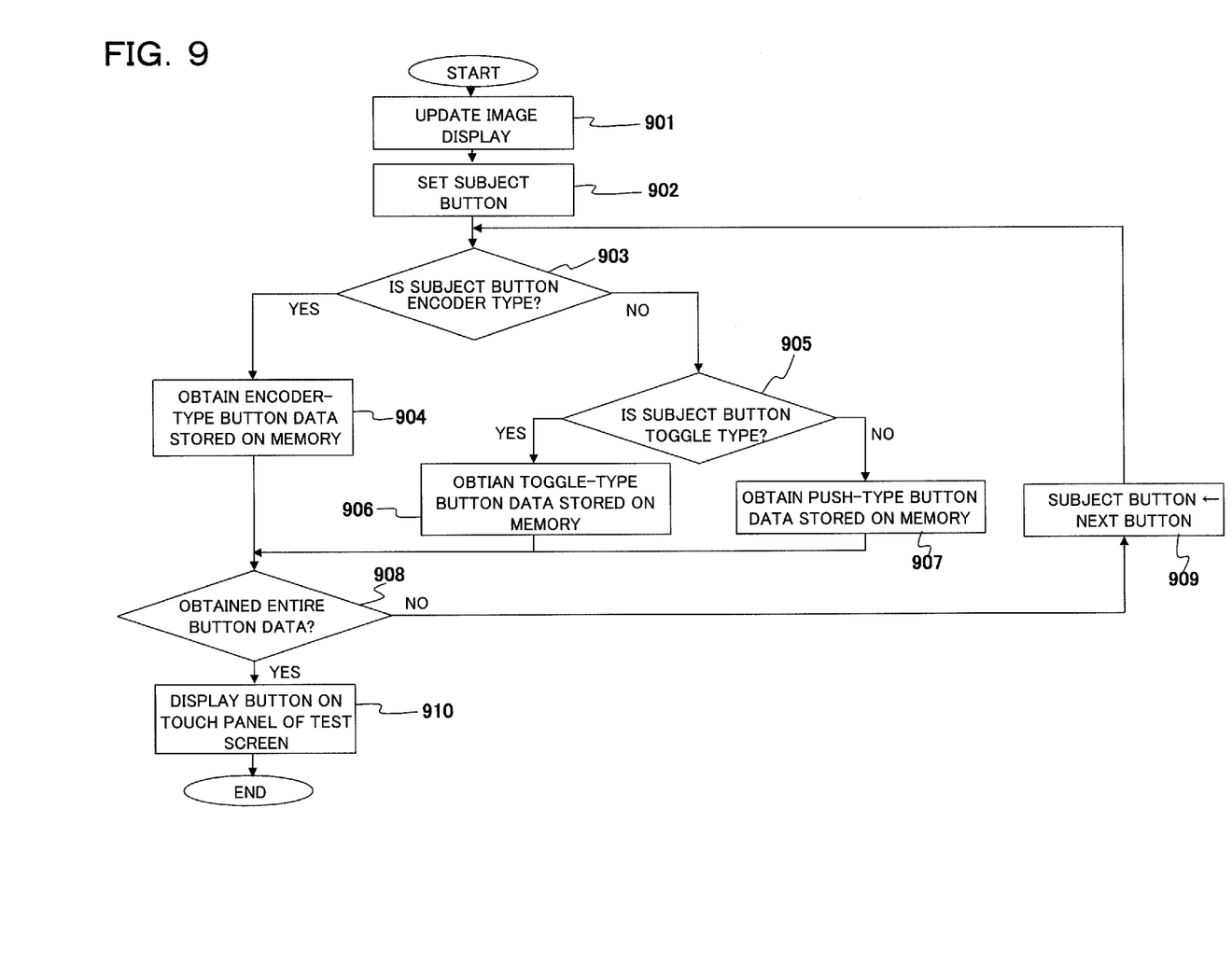
FIG. 9 is a flowchart for explaining an example of operation in the fourth embodiment.
Figure 10:
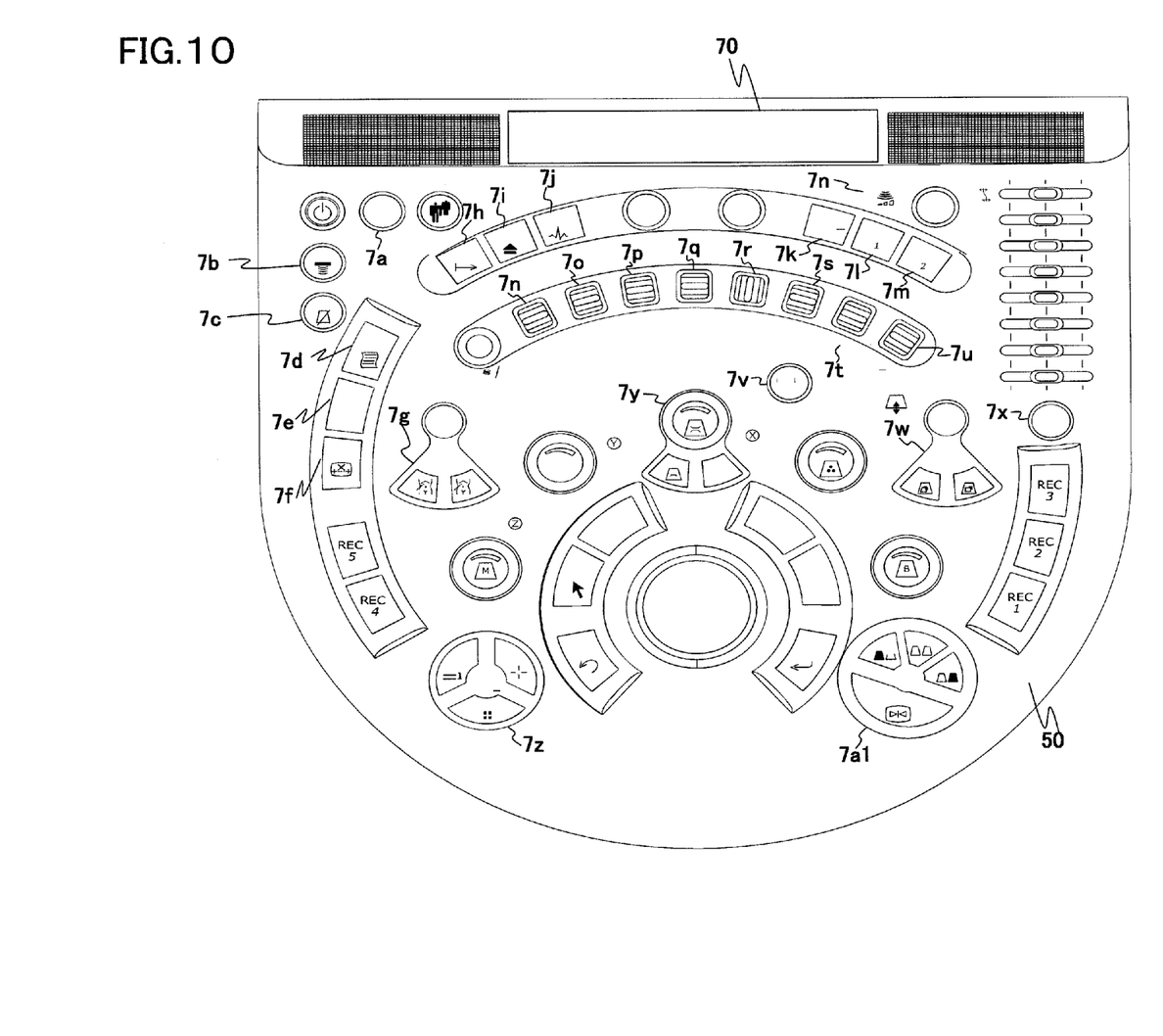
FIG. 10 is an enlarged view of a console shown in FIG. 2B.

This procedure is executed as shown in FIG. 9 by the program of a computer which configures control unit 60 and display control unit 80.

FIG. 9 is a flowchart for explaining an operation example of the fourth embodiment.

Control unit 60 executes image display update process of first display unit 100 and second display unit 70 (touch panel) (step 901).

The operator sets an object button to be displayed on second display unit 70 (touch panel) (step 902).

Control unit 60 determines whether the object button is the encoder-type button or not. If the determination result is yes step 904 is carried out, and if the result is no step 905 is carried out (step 903).

Control unit 60 acquires button-type data of the encoder type and the appended data thereto stored on storage unit (memory) 40 (step 904).

Control unit 60 determines whether the button type of the object button is the toggle type or not. If the determination result is yes step 906 is carried out, and if the result is no step 907 is carried out (step 905).

Control unit 60 acquires button-type data of toggle type and the appended data thereto stored on storage unit (memory) 40 (step 906).

Control unit 60 acquires button-type data of push type and the data appended data thereto stored on storage unit (memory) 40 (step 907).

Control unit 60 determines whether data of the entire object buttons is acquired or not. If data of the entire object buttons is acquired step 910 is carried out, and if not step 909 is carried out (step 908).

Control unit 60 switches the object button from the present one to the next one (step 909).

Control unit 60 causes display control unit 80 to display the button on second display unit 70 (touch panel) (step 910).

As described above, in accordance with the fourth embodiment, display control unit 80 sets the type of button switch for displaying the data on second display unit 70 based on the input condition of the first control parameter and to display the data by the set button switch on second display unit 70.

In this way, the operator can set the conditions by a command switch without changing his/her line of sight. Also, characteristic effect of the fourth embodiment is that since the operator can determine the operation object based on the button type of the menu, condition setting can be executed more intuitively.

Also, it is obvious that various kinds of alterations or modifications can be made within the scope of the technical idea disclosed in the embodiments of the present invention. For example, while the display unit is described as the first display unit and the second display unit in the above-described embodiments, one display unit may be divided into two display units. Also, while the control unit and the display control unit are separated in the above-described embodiments, the function of the display control unit may be provided to the control unit.

DESCRIPTION OF THE NUMERAL REFERENCES

10: probe, 20: ultrasonic image measuring unit, 50: input unit, 60: control unit, 70: second display unit, 80: display control unit, 100: first display unit, 106: body mark, 106e: measurement, 106f: hide trajectory, 106g: Ellipse Trace, 106i: region view, 106p: PW/CW, 106q: oblique inversion, 106r: simultaneous real, 106t: threshold value level, 106u: smoothing, 106v: automatic adjustment reset, 107b: SVolume, 107c: Volume, 107e: Histogram, 107f: Angle, 107g: Volume, 107l: move mark, 107n: mark; #, 107o: speaker volume, 107p: image division; #, 107r: user, 107s: flow invert, 107t: vertical split ratio, 107u: display setting, 107v: menu, 7a: examination-end button, 7b: probe, 7c: puncture guide, 7d: report, 7e: annotation, 7f: clear, 7g: probe mark, 7h: cue: 7i: eject, 7j: biological signal, 7k: image menu, 7l: function 1, 7m: function 2, 7n: sweep velocity, 7o: sample width, 7*p*: filter, 7*q*: base line, 7*r*: oblique, 7*s*: velocity range, 7*t*: frequency, 7*u*: focus, 7*v*: Fine Flow CFA, 7*w*: display depth, 7*x*: automatic adjustment, 7*y*: Doppler, 7*z*: measurement menu, 7*a*1: freeze

The invention claimed is:

1. An ultrasonic diagnostic apparatus comprising:
    a probe for transmitting ultrasonic waves to an object and receiving the reflected echo signals from the object;
    an ultrasonic image measuring unit for measuring an ultrasonic image, the ultrasonic image measuring unit being connected to the probe;
    a first display for displaying the ultrasonic image measured by the ultrasonic image measuring unit, the first display being connected to the ultrasonic image measuring unit; and
    a display control unit for controlling the first display and a second display, the display control unit being connected to the first display and the second display, and the second display comprising a function key,
    wherein the display control unit determines a first control parameter based on input by an operator, generates a menu for setting a second control parameter, which is to be next to the determined first control parameter, displays the menu to a part of the first display unit, and causes a switch on the second display unit to be displayed in correspondence with the generated menu.

2. The ultrasonic diagnostic apparatus according to claim 1, wherein the second display unit is configured to display the first control parameter or the second control parameter.

3. The ultrasonic diagnostic apparatus according to claim 1, wherein the display control unit sets a measurement menu including the distance, area and volume between predetermined points in an image as the first control parameter.

4. The ultrasonic diagnostic apparatus according to claim 1, wherein the display control unit sets a kind of a body mark as the first control parameter.

5. The ultrasonic diagnostic apparatus according to claim 1, wherein the display control unit sets a Doppler mode as the first control parameter.

6. The ultrasonic diagnostic apparatus according to ciaim 1, wherein the display control unit causes the display unit to display different types of button switches based on the first control parameter.

* * * * *